United States Patent
Larceri et al.

(10) Patent No.: US 9,636,848 B2
(45) Date of Patent: May 2, 2017

(54) DEVICE AND METHOD FOR THE PRODUCTION OF A COSMETIC PRODUCT FOR MAKE-UP

(71) Applicant: CHROMAVIS S.p.A., Milan (MI) (IT)

(72) Inventors: Nicola Larceri, Melegnano (IT); Fabio Moroni, Ripalta Cremasca (IT)

(73) Assignee: CHROMAVIS S.p.A., Milan (IT)

( * ) Notice: Subject to any disclaimer, the term of this patent is extended or adjusted under 35 U.S.C. 154(b) by 532 days.

(21) Appl. No.: 14/204,510

(22) Filed: Mar. 11, 2014

(65) Prior Publication Data

US 2014/0284831 A1 Sep. 25, 2014

(30) Foreign Application Priority Data

Mar. 19, 2013 (IT) .............................. MI2013A0419

(51) Int. Cl.
*B29C 33/44* (2006.01)
*A45D 40/16* (2006.01)
*B29C 43/34* (2006.01)
*A45D 33/00* (2006.01)
*B29C 43/20* (2006.01)
(Continued)

(52) U.S. Cl.
CPC .............. *B29C 33/44* (2013.01); *A45D 40/16* (2013.01); *B29C 43/34* (2013.01); *A45D 33/006* (2013.01); *A45D 33/18* (2013.01); *A45D 40/24* (2013.01); *A61K 8/0237* (2013.01); *B29C 43/18* (2013.01); *B29C 43/20* (2013.01); *B29C 43/203* (2013.01); *B29C 2043/181* (2013.01)

(58) Field of Classification Search
CPC ........ A45D 40/16; A45D 40/24; A45D 33/18; A45D 33/006; A61K 8/0237; B29C 33/44; B29C 43/18; B29C 43/20; B29C 43/203; B29C 2043/181
USPC ....................................... 425/436 R; 264/334
See application file for complete search history.

(56) References Cited

U.S. PATENT DOCUMENTS 4,403,932 A 9/1983 Ogasawara et al.

FOREIGN PATENT DOCUMENTS

JP 2012024282 A * 2/2012
KR 20110106511 A * 9/2011 ........... A61K 8/0237

OTHER PUBLICATIONS

Chol, KR 20110106511A, machine translation from Korean to English.*

(Continued)

*Primary Examiner* — Alison L Hindenlang
*Assistant Examiner* — Lawrence D Hohenbrink, Jr.
(74) *Attorney, Agent, or Firm* — King & Schickli, PLLC

(57) ABSTRACT

A device for accurately dosing cosmetic pastes in multicolor form on a base for the production of a cosmetic product for make-up, comprising a base element adapted to house a base, a mold which moves at least between an opening position and a closing position, said mold having at least one partition which divides a surface thereof facing the base element into at least two compartments, a peripheral element provided with walls which define an opening with shape similar to the perimeter shape of the mold and in which the mold is at least partially housed when it is in said closed position, said peripheral element being provided with at least two channels which run into said opening and protrude into it at least partially, the device providing means adapted to prevent the gluing of said cosmetic paste at least to the wall of the mold facing the base element.

16 Claims, 6 Drawing Sheets

(51) Int. Cl.
    *B29C 43/18*     (2006.01)
    *A45D 33/18*     (2006.01)
    *A61K 8/02*     (2006.01)
    *A45D 40/24*     (2006.01)

(56) References Cited

OTHER PUBLICATIONS

Tada et al., JP 2012024282A, machine translation from Japanese to English.*

* cited by examiner

US 9,636,848 B2

DEVICE AND METHOD FOR THE PRODUCTION OF A COSMETIC PRODUCT FOR MAKE-UP

This application claims the benefit of Italian Patent Application No. MI2013A000419 of Mar. 19, 2013, the disclosure of which is incorporated herein by reference.

FIELD OF THE INVENTION

The present invention refers to a device and a method for the production of a cosmetic product for make-up.

BACKGROUND

More specifically, it refers to a device for accurate dosing of cosmetic pastes in multicolour form on a base and a method for the production by means of said device of a multicolour baked tile product for make-up. It should be pointed out that the device and the method allow the dosing of multicolour pastes not in the form of melange, thus obtaining physically separate multicolour pastes on the base.

Currently multicolour baked tile make-up products are produced by hand.

The manufacturing process of said products entails positioning a pre-determined quantity of cosmetic paste with a viscosity of approximately 1,000,000 cP (Centipoise) on a base. The base is then placed in a press provided with a mould able to shape the cosmetic paste by compressing it. For example the cosmetic paste takes on a dome shape and is distributed over the whole surface of the base, if it has a circular form.

Once this phase has been completed, a shaped blade is used which is plunged into the paste until it comes into contact with the base. The blade is then translated horizontally, allowing the removal of part of the cosmetic paste. Part of the base is thus without paste, while the other part is covered by a cosmetic paste previously shaped by the mould, for example in the form of a dome.

The next step of the process entails dosing on the exposed part of the base a further quantity of cosmetic paste, different from the first in terms of colour, properties or other characteristics.

The pastes (both old and new) are pressed again with the mould used previously which shapes the new paste according to its form, while it leaves the paste previously arranged on the base substantially unchanged as its shape already corresponds to that of the mould.

The process is thus repeated as required until the desired number of cosmetic pastes are arranged on the base.

The product thus shaped is dried for the time necessary to evaporate the volatile component present in the paste, which thus takes a more solid consistency.

The current production method is substantially manual. It entails a great number of steps and therefore takes a very long time, it is costly and requires the training of skilled operators who are able to accurately remove the paste from the base according to clear well-defined lines.

A further drawback of the method described above is that a large quantity of cosmetic paste is wasted. In fact, the residual paste which is removed from the base by means of the blades is inevitably lost.

SUMMARY

The object of the present invention is therefore to provide a device and a method able to automate the production process of the multicolour baked cosmetic, therefore making it quicker and cheaper, and at the same time avoiding the wastage of large quantities of cosmetic product.

These and other objects are achieved by producing a device and method for the production of a cosmetic product for make-up, according to the technical teachings of the attached claims.

Advantageously the method described here allows the production of a baked product with an attractive surface finish and an aesthetically pleasing decoration.

BRIEF DESCRIPTION OF THE DRAWINGS

Further characteristics and advantages of the invention will become evident from the description of a preferred but not exclusive embodiment of the device for dosing cosmetic pastes preferably in multicolour form in order to produce a cosmetic product for make-up, illustrated by way of non-limiting example in the attached drawings in which.

DETAILED DESCRIPTION

Figure 1:
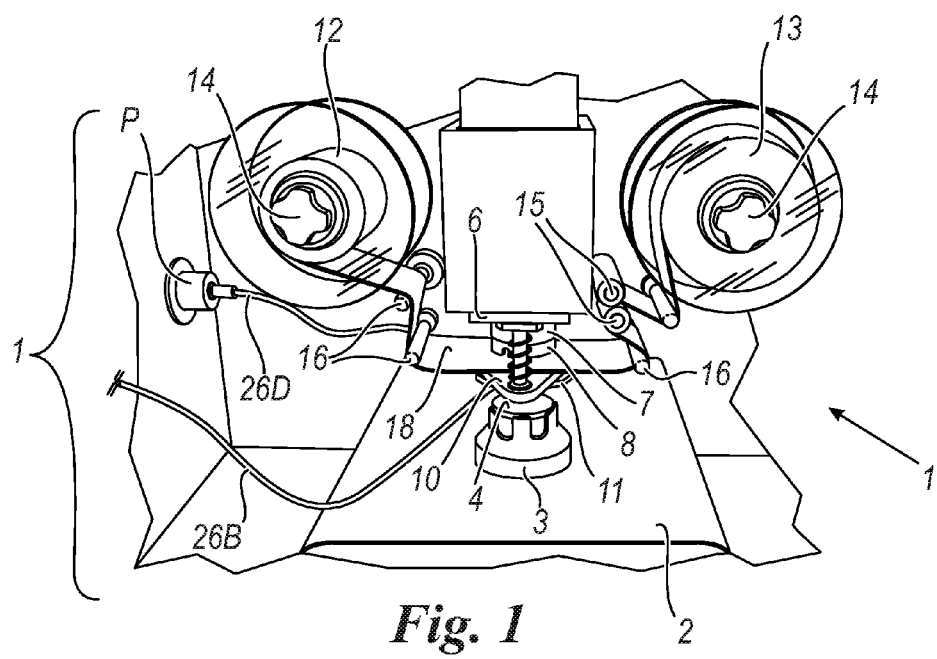
FIG. 1 is a simplified perspective view of a device according to the present invention.

With reference to the figures cited, a device is shown for dosing cosmetic pastes preferably in multicolour form in order to produce a cosmetic product for make-up indicated overall by the reference number 1.

It should be underlined that the device allows dosing of multicolour pastes not in melange form but in order to obtain multicolour pastes which are physically separate on the base.

The cosmetic product produced is a multicolour baked tile product which originates from a paste wetted with suitable volatile solvents, in particular water.

It comprises a resting surface 2 to which a base element 3 is fixed. The base element is preferably a shaped metal element, able to provide a support for a base on which the cosmetic paste will be arranged.

In the example illustrated, the base 4 is made of terracotta and has a circular shape. Consequently the base element 3 has a surface 3A and a plurality of protruding edges 3B arranged in a circle. As can be seen, the protruding edges are positioned so as to create a containment edge for the base, thus preventing lateral movement thereof, but allowing easy positioning and removal. In said regard the edge is provided with openings 5 which facilitate extraction of the base by fingers.

The openings 5 made in the edge also have a further function which will become clear below.

It should be noted that when the base is supported by the base element, it protrudes from it at the top, thus presenting an upper surface 4A completely exposed at the top.

Above the base element a mobile element 6 of a press is provided, to which a first cylindrical support 7 is fixed that can carry a removable mould 8.

The element 6 furthermore supports a second plate support 10 in a sliding manner on guides 9 and in contrast to springs 9A. A peripheral element 11 is removably fixed to the second support.

The device comprises feeding means for feeding a cloth 18 which comprise supporting cylinders 14 supporting a reel or roll of new cloth 12 and a reel of used cloth 13. Tensioning rollers for tensioning the cloth 15 and relay rollers for the same are also provided.

The various components of the feeding means are arranged so as to pass the cloth 18 between the mould 8 and the peripheral element 11 (i.e. between the mould and the second support 10 or plate).

The mould 8 of the device 1 (which can be seen clearly in FIGS. 5 and 6A) has a surface (or top) facing towards the base element with convex dome shape and in this specific case is circular in plan since the mould is used with a circular base. The mould can have a different shape, however, corresponding to that of the base (this will be discussed below).

As can be seen, the mould 8 has a plurality of partitions 20, in this specific case four, i.e. a first 20A, a second 20B, a third 20C and a fourth partition 20D which divide the surface of the mould into five compartments 21A-E (from the first to the fifth compartment).

As can be noted, the mould is also provided with apertures 22A-E in its lateral surface which allow access to said compartments.

The peripheral element 11 is provided with walls which define an opening 23 with shape similar to the perimetral shape of the mould 8. Substantially, the mould has a shape such that it can freely run in the opening 23 of the peripheral element without friction.

The peripheral element 11 is provided with a plurality of holes 24 with number corresponding to that of the mould compartments (and therefore five in this case) in each of which one channel can be housed which leads into the opening 23 and preferably protrudes into it at least partially. In the case in question, the at least one channel may be formed of a simple tube or rubber tube 26 which is preferably transparent but which can be obtained directly in a single piece with the peripheral element.

Figure 2:
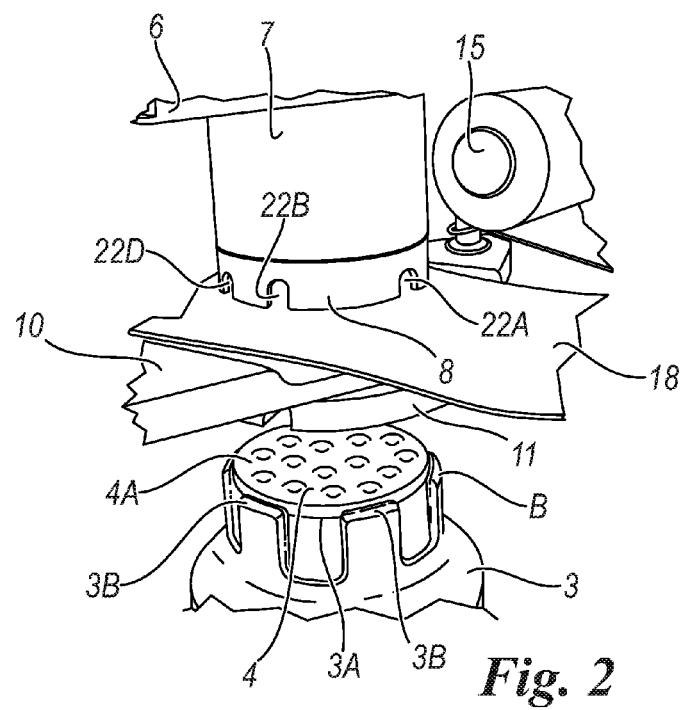
FIG. 2 and FIG. 3 are detailed views of parts of the device of FIG. 1.
Figure 3:
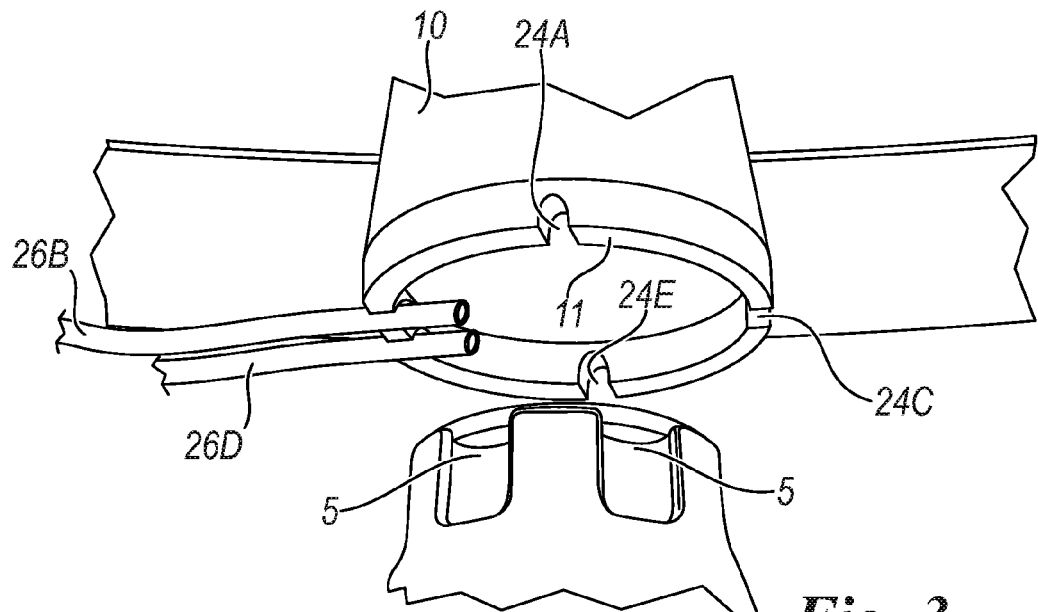
Figure 4:
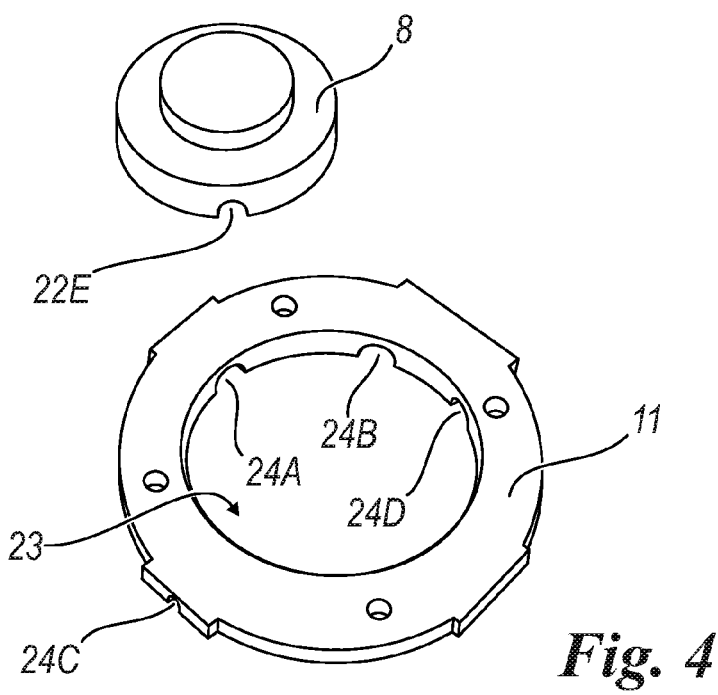
FIG. 4 is a perspective view from above of a mould and a peripheral element decoupled which are part of the device of the present invention.

The mobile element 6 which supports the mould and the peripheral element move between an open position (shown in FIGS. 1, 2 and 3) in which the mould and the peripheral element are distant from the base element (and consequently from the base when it is on the base element) and a closed position in which they are lowered onto the base element (i.e. onto the base).

When the mobile element 6 is lowered, the second support 10 drops towards the base element together with the peripheral element. It rests on the protruding edges 3B of the base element 3, the springs 9A are compressed and the mould 8 continues to move down until it rests on the base 4.

Figure 5:
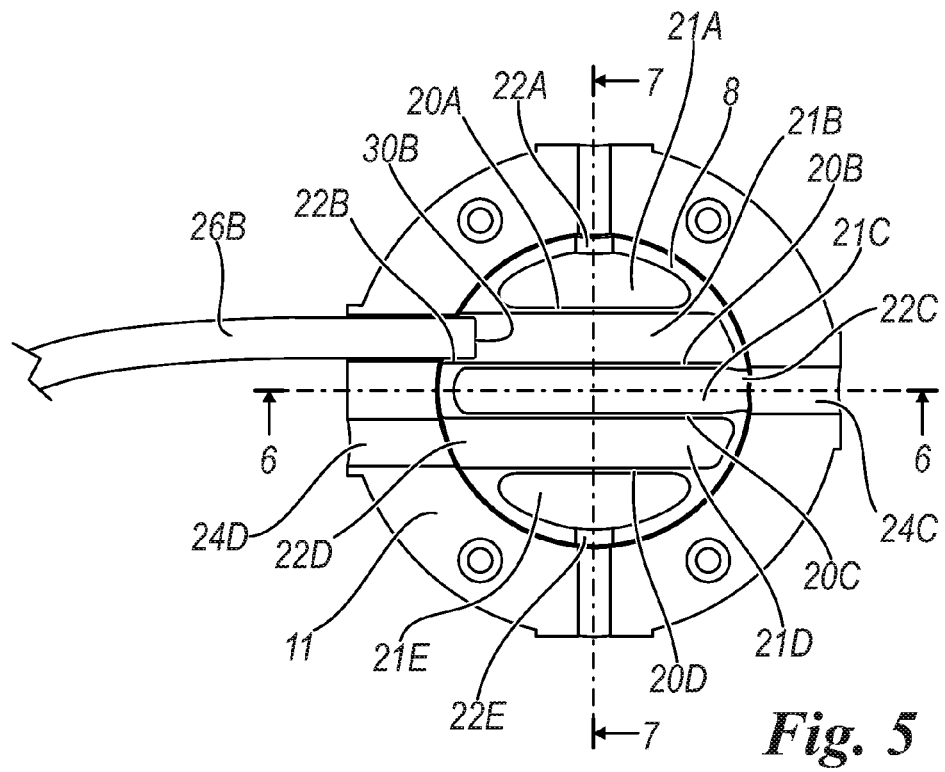
FIG. 5 is a view from below of the mould and the peripheral element when they are mutually coupled and in the position which they assume during closing on a base.
Figure 6A:
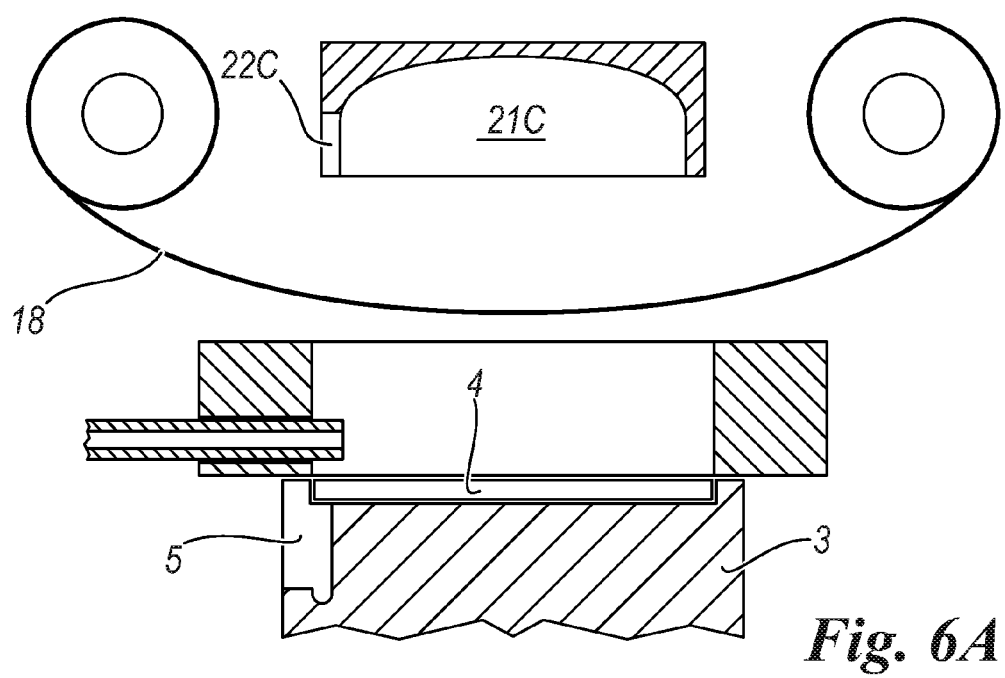
FIG. 6A and FIG. 6B are simplified sections taken along the line 6-6 of FIG. 5, when the mould is mounted on the device, the first in an opening position of the mould and the second in a closing position.

In said closed position, the mould and the peripheral element are positioned as in FIG. 5, but with the cloth 18 interposed between them. At each closing of the mould, clean cloth is used which is moved preferably automatically by means of the tensioning rollers 15 mentioned previously.

In particular FIG. 5 shows by way of example a single rubber tube 26B inserted in the hole 22B and intended to fill the compartment 21B with cosmetic paste 30B; in use, each hole of the peripheral element is associated with the relative tube. Substantially, with the mould closed, the part of the mould 8 visible in FIG. 5 rests on the base and therefore the base and the mould compartments form areas which will be filled with paste.

It should be noted that the apertures 22A-E present in the mould allow the latter to rest on the base 11 without deforming the tubes 26 which protrude into the opening of the peripheral element. In fact, the apertures correspond exactly to the tubes when the mould is closed.

The operation for filling the mould compartments can be better understood from an analysis of the sections of FIGS. 6A, 6B, 7A and 7B which are taken along the section lines indicated in FIG. 5, in two operating phases of the device when the mould and the peripheral element are mounted on the device 1.

Substantially when the mould is in the closed position (FIG. 7B—note that in this figure the cloth is not shown for the sake of simplicity), cosmetic paste is introduced via the tube 26B, filling the compartment 21B, delimited at the bottom by a portion of the base 4.

This takes place substantially simultaneously for all the compartments which are filled by the respective tube.

Figure 6B:
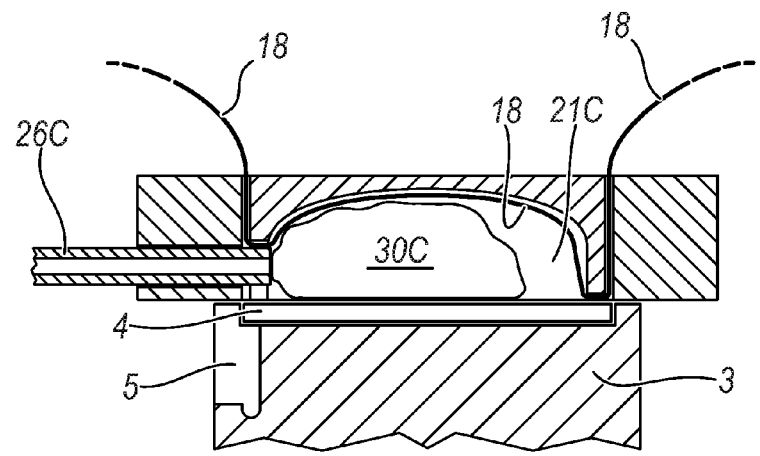
Figure 7A:
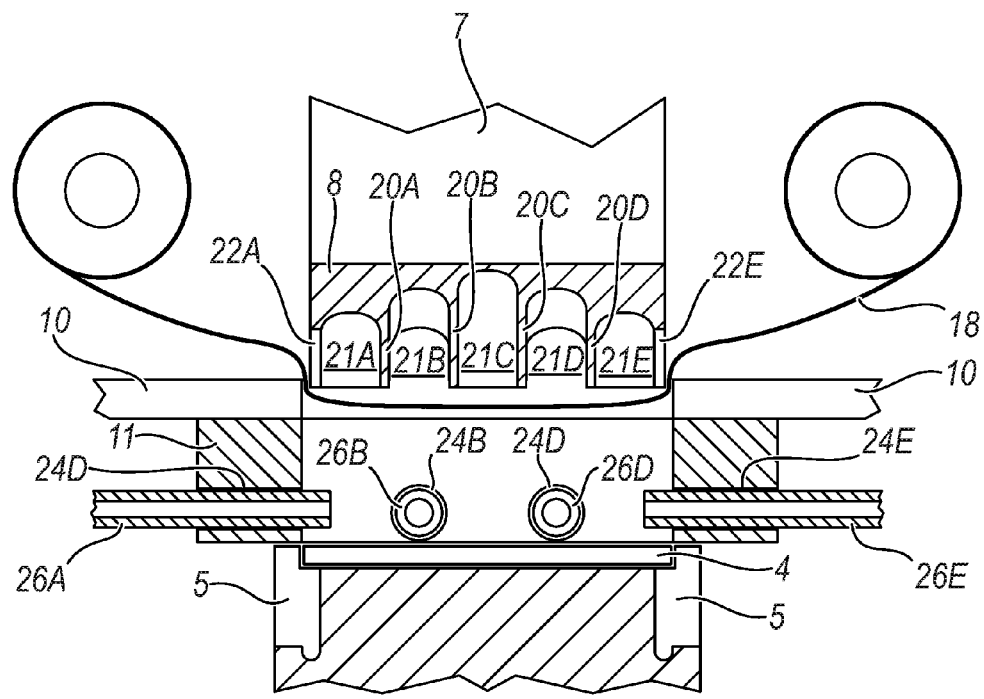
FIG. 7A and FIG. 7B are simplified sections taken along the line 7-7 of FIG. 5, when the mould is mounted on the device, the first in an opening position of the mould and the second in a closed position.
Figure 7B:
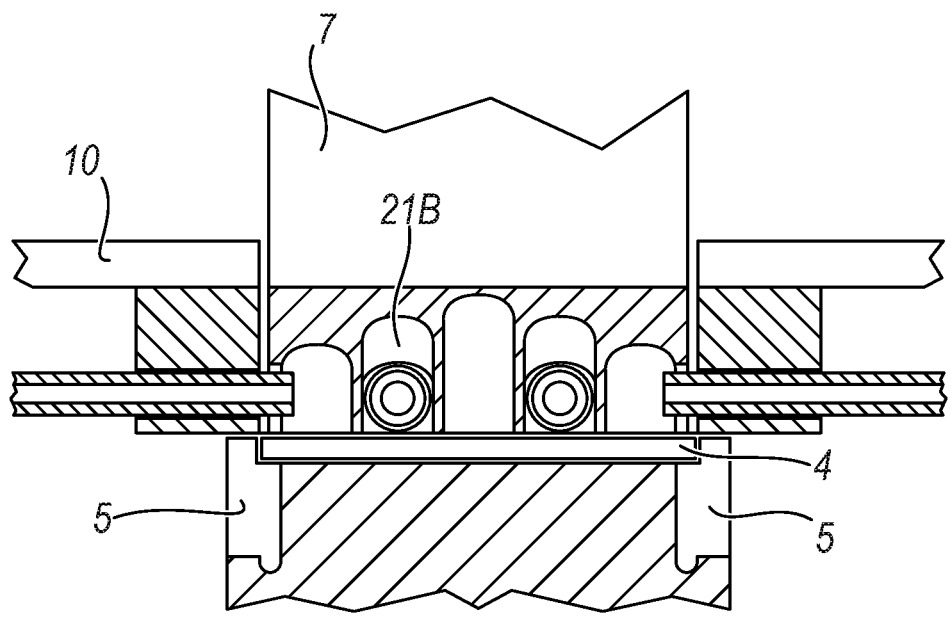

FIG. 6B shows a phase in which a tube 26C intended to fill the compartment 21C introduces cosmetic paste 30C into the latter. It can be seen that the cloth 18 is pressed onto the surfaces of the mould by the paste which is introduced into the compartment.

Figure 8:
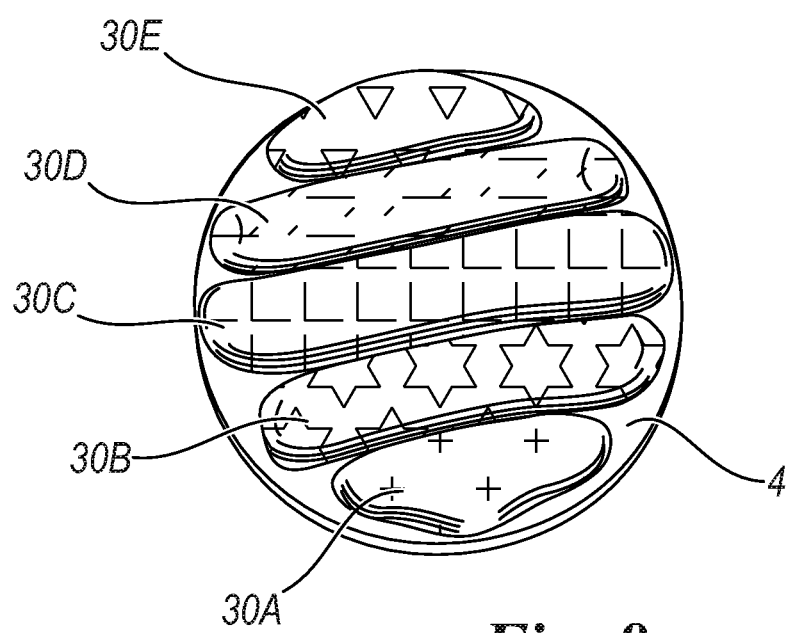
FIG. 8 is a view of a semi-finished product which is produced by the device of FIG. 1, by means of the mould of FIG. 5.

Once the compartments have been filled with the predetermined quantity of cosmetic paste 30A, 30B, 30C, 30D and 30E, which if necessary can slightly overflow into the openings 5 of the base element, the mould is raised and a semi-finished product is obtained like the one shown in FIG. 8.

The cloth 18 which covers the surfaces of the mould facilitates detachment of the paste and the mould itself. As can be seen, on the base the paste takes the shape of the compartments and is 'attached' to the latter.

It should be noted that the paste introduced into the various mould compartments can have different characteristics (for example colour) and therefore each of the tubes is preferably fed by a different source of paste.

In the example considered, the five compartments are fed with a cosmetic paste which has the same characteristics and differs for each tube only in terms of colour. Therefore each tube introduces into the mould a paste of different colour. Preferably the paste used to produce the cosmetic by means of the device described has a dynamic viscosity at 25° C. between 800,000 cP (Centipoise) and 1,500,000 cP, preferably 1,200,000 cP.

According to another definition, the paste must have a viscosity that allows it to take the shape given by the mould and keep this shape also when the mould is removed from the base.

The pressure at which it is fed to the compartments is very low, therefore it is more like a dosing of the paste into the compartments. By way of example, the paste is subjected to a maximum pressure of between 5 and 20 bar.

It is introduced into the tubes by means of a pump, preferably of the screw type. The use of said pump allows perfect dosing of the quantity of paste introduced into the compartments and furthermore it does not compress or "squeeze" the paste, maintaining its physical characteristics unchanged. The use of a screw pump is particularly advantageous since the paste is not 'stressed' and any pearls or other fragile elements present in the same are not broken as would happen with a traditional reciprocating pump.

In the drawings, for the sake of simplicity of description, some tubes and sometimes the cloth 18 are not shown, but in actual use of the device, each tube is housed in the relative hole of the peripheral element and the cloth is always present between the mould and the peripheral element.

When the mould is opened, a semi-finished product is obtained formed of a base on which the paste is arranged having the shape of the mould compartments, like the one shown in FIG. 8. It is to be noted that at this point the paste maintains the shape given by the mould.

Figure 9:
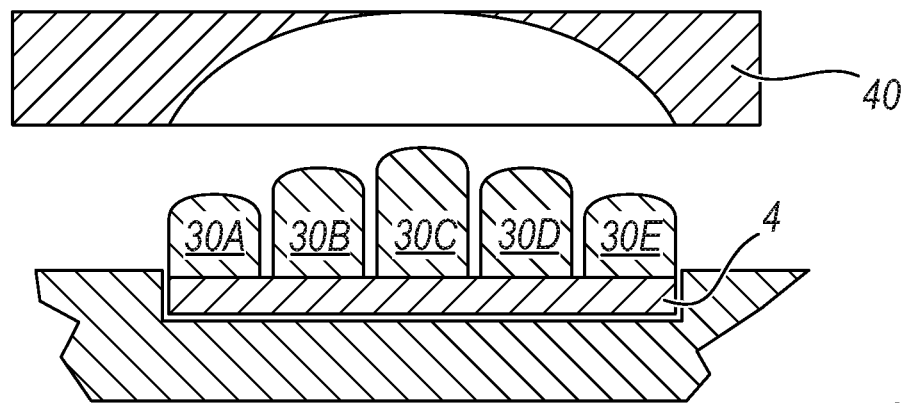
FIG. 9 shows in cross section a work phase of the semi-finished product of FIG. 8.
Figure 10:
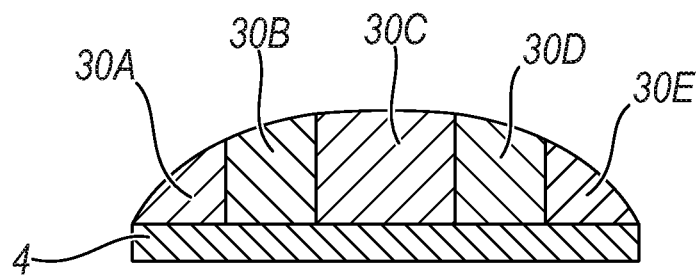
FIG. 10 shows a cross section of the finished product which is obtained following the work process shown in FIG. 9.

Subsequently the semi-finished product is removed from the base element by means of the openings 5, and undergoes a further processing phase, this time conventional, using a simple press. This phase is shown in FIG. 9 and a further mould is lowered onto the semi-finished product so that it takes on the final shape of FIGS. 10 (in section) and 11.

Figure 11:
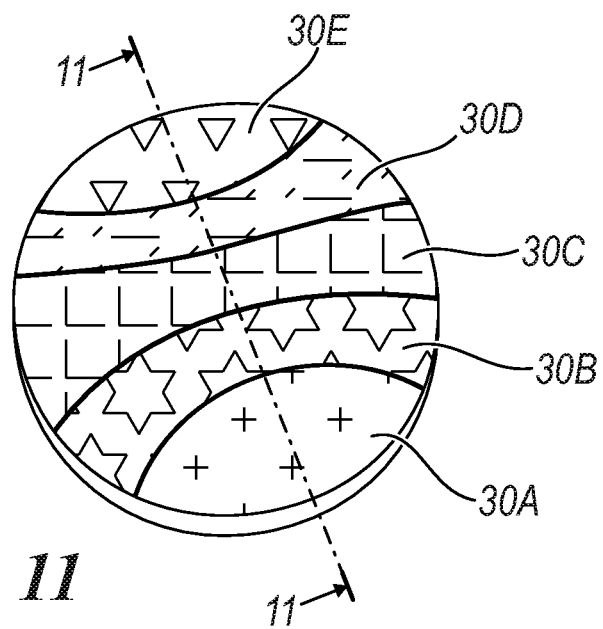
FIG. 11 shows in a perspective view from above the finished product which is obtained following the work process shown in FIG. 9.

Said work phase, which is in effect a compression of the paste by means of a further mould 40, has the purpose of eliminating the vacuums created by the mould partitions and giving the paste a substantially final external shape like the one shown in FIG. 11.

Subsequently the base with the appropriately shaped paste is dried for a pre-set time.

Different drying times are required according to the drying methods. For example, oven drying at 60° C. requires 10 h to 24 h, preferably 20 h.

Substantially, the paste is dried until it has a solvent content between 0.5 and 1.5%, preferably 0.8% by weight. The solvent used to produce the paste is of conventional type, for example water or volatile silicon.

In the embodiment described, the further mould has a surface designed to come into contact with the completely smooth cosmetic paste but it can also have a surface with ridges and hollows so as to impart a pre-determined motif to the surface of the paste, which is thus decorated. Also in this case a cloth is used (not shown) to facilitate opening of the further mould.

Obviously in the preceding description reference is made to one embodiment of the device. Many parts, in particular the moulds and the base element, can have different configurations.

Firstly the mould used can have a different number of partitions and therefore compartments. Obviously the minimum number will be one partition, resulting in one mould with two compartments. In said case the peripheral element will have only two holes with two tubes or channels which will each feed a compartment.

There may be any number of compartments and partitions. The partitions may have any type of development, for example in the shape of a C, S or other.

Furthermore it is not necessary to feed different paste to each tube, given that within the same cosmetic product the same paste could also be used in different positions.

The drawings and the description refer to a terracotta base of circular shape. Obviously bases (and consequently moulds and base elements) can be used adapted to form cosmetic products with base of any shape, for example square, elliptical, rectangular etc.

In the embodiment described, furthermore, the tops of the first and second mould have a concavity. However, they could be flat, knurled, with bosses, brands, logos etc., according to the surface shape of the cosmetic to be produced.

Obviously base element, shape of the peripheral element opening and shape of the mould will vary according to the base used.

For this reason, both the mould and the peripheral element and also the base element are removably mounted on the device and easily interchanged.

The base can be made of any material adapted to contain a product for make-up, for example in metal, plastic or other material. It may or may not have a lateral containment edge.

In the example described the mould and the peripheral element are made of plastic, for rapid prototyping, but they can be made of any other material suitable for the purpose.

Furthermore other means (different from the cloth) may be provided adapted to prevent gluing of said cosmetic paste at least to the wall of the mould facing the base element, for example a particular polishing or surface treatment of the mould (teflon or similar) designed to come into contact with the paste. In this way, use of the cloth as an anti-gluing means could be avoided.

One embodiment of the invention has been illustrated, but others can be conceived, exploiting the same inventive concept.

The invention claimed is:

1. Device for producing a cosmetic product for make-up, with pasty consistency during the processing phase, comprising:
   a. a base element adapted to house a base;
   b. a mould moving at least between an open position in which the mould is spaced from the base element and a closed position in which the mould is lowered onto the base element, said mould having at least one partition which divides a surface thereof facing the base element into at least two compartments;
   c. a peripheral element provided with walls which define an opening with shape similar to the perimeter shape of the mould and in which the mould is at least partially housed when the mould is in said closed position;
   d. said peripheral element being provided with at least two channels which lead into said opening and protrude into said opening at least partially;
   e. the mould being provided with apertures on a lateral surface corresponding to said channels so that, when the mould is in the closed position, each of said channels can convey a different cosmetic paste for make-up into the respective compartment;
   f. the device being provided with means adapted to prevent the gluing of said cosmetic paste at least to the wall of the mould facing the base element.

2. Device according to claim 1 wherein said means adapted to prevent gluing comprise a cloth which, when the mould is in the closed position, is interposed between the mould and the peripheral element.

3. Device according to claim 1 wherein automatic means are provided for positioning a clean part of cloth between the mould and the peripheral element each time the mould closes.

4. Device according to claim 1 wherein the mould is secured to a mobile element which supports, translatable counter to at least one elastic element, a supporting plate for the peripheral element.

5. Device according to claim 2 wherein said cloth, during use, is interposed between said mobile element and said supporting plate.

6. Device according to claim 1 wherein said base element is provided with a containment wall for said base, the wall having openings to allow the paste introduced into each compartment to overflow towards them once each compartment has been filled.

7. Device according to claim 1 wherein the mould is provided with a plurality of compartments, each fed by at least one channel of the peripheral element.

8. Device according to claim 1 wherein the channels are fed with paste by means of a screw pump.

9. Device according to claim 1 wherein the wall of the mould facing the base element has a convex configuration.

10. Method for producing a cosmetic product for make-up comprising the steps of:
   a. arranging a base on a base element;
   b. preparing a mould which has at least one partition which divides a surface thereof facing the base into at least two compartments and a peripheral element provided with walls which define an opening of shape similar to the perimeter shape of the mould, the peripheral element being provided with at least two channels which lead into said opening and protrude into said opening at least partially, the mould being provided with apertures in a lateral surface corresponding to the channels of the peripheral element;
   c. moving the mould and the peripheral element towards the base and the base element, until the mould is inserted in the opening of the peripheral element and rests on the base;
   d. introducing into each of said channels a different cosmetic paste for make-up until each channel has filled the respective compartment;
   e. moving the mould away from the base and subsequently also moving the pheripheral element away;
   f. preventing said cosmetic paste from gluing at least to a wall of the mould facing the base element;
   g. taking from the base element the base on which the cosmetic paste is arranged, conveyed onto it by the channels, and having the shape of the mould compartments;
   h. pressing the cosmetic paste with a further mould to compress said paste so as to eliminate the vacuums created by the at least one partition of the mould and give the paste a substantially final external shape, and
   i. drying the paste for a set time.

11. Method according to claim 10 wherein before moving the mould and the peripheral element towards the base and the base element, a clean cloth is interposed between the mould and the peripheral element, proceeding to the next step without removing the cloth.

12. Method according to claim 10 wherein the peripheral element is lowered until it comes into contact with the base element.

13. Method according to claim 10 wherein the further mould has a surface designed to come into contact with the cosmetic paste which is completely smooth and/or has a surface with ridges and hollows so as to impart a pre-determined motif to the surface of the paste, which is thus decorated.

14. Method according to claim 10 wherein the paste is dried until it has a solvent content between 0.5 and 1.5%, preferably 0.8% by weight.

15. Method according to claim 10 wherein said paste has a dynamic viscosity at 25° C. between 800,000 cP and 1,500,000 cP, preferably 1,200,000 cP.

16. Device for producing a cosmetic product for make-up, with pasty consistency during the processing phase, comprising:
   a. a base element adapted to house a base;
   b. a mould moving at least between an open position in which the mould is spaced from the base element and a closed position in which the mould is lowered onto the base element, said mould having at least one partition which divides a surface thereof facing the base element into at least two compartments;
   c. a peripheral element provided with walls which define an opening with shape similar to the perimeter shape of the mould and in which the mould is at least partially housed when the mould is in said closed position;
   d. said peripheral element being provided with at least two channels which lead into said opening and protrude into said opening at least partially;
   e. the mould being provided with apertures on a lateral surface corresponding to said channels so that, when the mould is in the closed position, each of said channels can convey a different cosmetic paste for make-up into the respective compartment;
   f. the device being configured to prevent the gluing of said cosmetic paste at least to the wall of the mould facing the base element.

* * * * *